US008642007B2

(12) United States Patent
Kong et al.

(10) Patent No.: US 8,642,007 B2
(45) Date of Patent: Feb. 4, 2014

(54) METHOD AND COMPOUND FOR TREATMENT OF CANCER USING PHOSPHOROUS-32 LABELED DNA

(76) Inventors: Yanping Kong, Merrimack, NH (US); Jinhong Liu, Merrimack, NH (US)

( * ) Notice: Subject to any disclaimer, the term of this patent is extended or adjusted under 35 U.S.C. 154(b) by 158 days.

(21) Appl. No.: 12/886,127

(22) Filed: Sep. 20, 2010

(65) Prior Publication Data

US 2012/0070373 A1    Mar. 22, 2012

(51) Int. Cl.
*A61K 51/00*     (2006.01)
*C07H 21/04*     (2006.01)
*A61P 35/00*     (2006.01)

(52) U.S. Cl.
USPC ........................................ 424/1.73; 536/23.1

(58) Field of Classification Search
None
See application file for complete search history.

(56) References Cited

U.S. PATENT DOCUMENTS

| | | | |
|---|---|---|---|
| 6,060,458 A | 5/2000 | Moschel et al. | |
| 6,159,142 A | 12/2000 | Alt | |
| 6,310,195 B1 | 10/2001 | Colucci et al. | |
| 6,531,512 B1 | 3/2003 | Kramer et al. | |
| 6,552,005 B1 | 4/2003 | Buchsbaum et al. | |
| 6,599,909 B1 | 7/2003 | Buchsbaum et al. | |
| 6,689,561 B1 | 2/2004 | Carson et al. | |
| 6,703,375 B2 | 3/2004 | Buchsbaum et al. | |
| 7,011,812 B1* | 3/2006 | Griffiths et al. | 424/1.49 |
| 7,179,912 B2 | 2/2007 | Halbrook et al. | |
| 7,473,561 B2 | 1/2009 | Langenfeld | |
| 2004/0067197 A1 | 4/2004 | Leclerc et al. | |

FOREIGN PATENT DOCUMENTS

| | | |
|---|---|---|
| WO | 9823299 A2 | 6/1998 |
| WO | 2006096754 A2 | 9/2006 |
| WO | 2008126837 A1 | 10/2008 |

OTHER PUBLICATIONS

He et al. (World Journal of Gastroenterology, 2004; 10(5): 660-663).*
Silberstein et al. (Seminars in Nuclear Medicine. Jan. 1992; 22(1):17-27).*
Hamoudeh et al (Advanced Drug Delivery Reviews 2008; 60:1329-1346).*
Lee et al. (Hepatology 2004; 40: 667-676).*
Duffy. Clinical Chemistry. 2011; 47(4): 624-630.*
Doi, et al., "Ablation of the Thyroid Remnant and I-131 Dose in a Differentiated Thyroid Cancer: A Meta-Analysis Revisited", "Clinical Medicine & Research", Jun. 2007, pp. 87-90, vol. 5, No. 2, Published in: US.
Malumbres, et al., "CDK Inhibitors in Cancer Therapy: What is Next?", "Trends in Pharmacological Sciences", Jan. 2008, pp. 16-21, vol. 29, No. 1, Publisher: Elsevier, Ltd., Published in: US.

Kong, et al., "An Efficient In Vivo Recombination Cloning Procedure for Modifying and Combining HSV-1 COSMIDS", "Journal of Virological Methods", Jul. 1999, pp. 129-136, vol. 80, No. 2, Publisher: Elsevier Science, Published in: US.
Hwang, et al., "Gene Therapy for Primary and Metastatic Pancreatic Cancer With Intraperitoneal Retroviral Vector Bearing the Wide-Type P", "Surgery", Aug. 1998, pp. 143-151, vol. 124, No. 2, Published in: US.
Ozols, "Maintenance Therapy in Advanced Ovarian Cancer: Progression-Free Survival and Clinical Benefit", "Journal of Clinical Oncology", Jul. 1, 2003, pp. 2451-2453, vol. 21, No. 13, Published in: US.
Keedy, et al., "Phase I Study of Adenovirus P53 Administered by Bronchoalveolar Lavage in Patients With Bronchioloalveolar Cell Lung Car", "Journal of Clinic! Oncology", Sep. 1, 2008, Publisher: American Society of Clinical Oncology, Published in: US.
McLaren, et al., "Radioactive Phosphorus (P32) in Treatment of Menorrhagia", "British Medical Journal", Feb. 14, 1953, pp. 358-363.
Van Nostrand, et al., "Radioiodine in the Treatment of Thyroid Cancer", "Endocrinology and Metabolism Clinics of North America", Sep. 2007, pp. 807-822, vol. 36, No. 3, Publisher: Elsevier Saunders, Published in: US.
Vedel, et al., "Changes in Methylation Pattern of Albumin and A-Fetoprotein Genes in Developing Rat Liver and Neoplasia", "Nucleic Acids Research", , pp. 4335-4354, vol. 11, No. 13, Publisher: IRL Press Limited, Published in: UK (1983).
Colle, "Chemical Digestion and Radionuclidic Assay of TiNi-Encapsulated 32P Intravascular Brachytherapy Sources", "Applied Radiation and Isotopes", May 1, 1999, pp. 811-833, vol. 50, No. 5, Publisher: Pergamon, Published in: US.

(Continued)

*Primary Examiner* — Scott Long
(74) *Attorney, Agent, or Firm* — Loginov & Sicard; William A. Loginov

(57) ABSTRACT

This invention provides a combination of a gene and isotope therapy that is applied to a cancerous tissue to selectively kill that associated cancer cells with minimal negative effects on surrounding non-cancerous cells. Functionally, the specific DNA fragments with labeled isotope are able to bind the tumor cells DNA through recombination, and then the isotope kills the tumor cells. A gene is employed as a carrier to deliver the P-32 which can kill cancer cells through radioactive emission. Unlike traditional gene therapy, which employs a gene to express a protein, which can suppress the cancer cell growth or increase the sensitivity for radiation therapy or chemotherapy, the illustrative embodiment actually binds the radioactive substance via a gene. The illustrative embodiment produces the compound/agent containing a gene (DNA fragment) and P-32 through use of conventional P-32 labeling techniques such as those employed in molecular biology experiments (for example experiments used to test gene expression and gene amplification potency). In the illustrative embodiment, however, the same P-32 labeled DNA is employed directly for cancer treatment through a novel medical treatment method. Appropriate doses are provided to patients as part of a medical treatment method.

10 Claims, 3 Drawing Sheets

(56) References Cited

OTHER PUBLICATIONS

Liao, et al., "Cloing of Rat A-Fetoprotein 3'-Terminal Complementary Deoxyribonucleic Acid Sequences and Preperation of Radioactively Labeled Hybridization Probes from Cloned Deoxyribonucleic Acid Inserts", "Biochemistry", , pp. 1646-1652, vol. 20, No. 6, Publisher: American Chemical Society, Published in: US (1981).

Yue, et al., "Dosimetry Calculation for a Novel Phosphorus-32-Impregnated Balloon Angioplasty Catheter for Intravascular Brachytherapy", "Cardiovascular Radiation Medicine", Oct. 1, 1999, pp. 349-357, vol. 1, No. 4, Publisher: Elsevier, Published in: US Frain, et al., "Hormonal Control of Alpha-Fetoprotein Gene Expression in Developing Rat Liver. Evidence for a Selective Action of Glucocorticoids at the Transcriptional Level", "Annales d'Endocrinologie", Oct. 1982, pp. 370-383, vol. 43, No. 5, Publisher: Masson, Published in: FR.

He, et al., "Preparation and Characteristics of DNA-Nanoparticles Targeting to Hepatocarcinoma Cells", "Work Journal of Gastroenterology", Mar. 1, 2004, pp. 660-663, vol. 10, No. 5, Publisher: The WJG Press.

Lucotte, et al., "Restriction-Site Polymorphism of the Albumin and the Alpha Fetoprotein Genes in Two Inbred Strains of Rats", "Biochemical Systematics and Ecology", May 16, 1984, pp. 225-230, vol. 12, No. 2, Publisher: Pergamon Press Ltd., Published in: UK.

He, et al., "Study on In Vivo Distribution of Liver-Targeting Nanoparticles Encapsulating Thymidine Kinase Gene (TK Gene) in Mice", "Journal of Materials Science: Materials in Medicine", Jul. 10, 2007, pp. 559-565, vol. 19, No. 2, Publisher: Springer Scienc + Business Media LLC, Published in: US.

* cited by examiner

METHOD AND COMPOUND FOR TREATMENT OF CANCER USING PHOSPHOROUS-32 LABELED DNA

FIELD OF THE INVENTION

This invention relates to cancer treatments and medications and more particularly to treatments and medications associated with gene therapy.

BRIEF DESCRIPTION OF THE SEQUENCE LISTING

Incorporated herein by reference in its entirety is a Sequence Listing, comprising SEQ ID NO: 1 to SEQ ID NO: 4. The Sequence Listing is filed electronically via the United Stated Patent Office Electronic Filing System (EFS) as a computer-readable ASCII (.txt) file named "KongSequence0001.txt", created on Nov. 5, 2010 and of 884 bytes in size.

BACKGROUND OF THE INVENTION

Cancer is an abnormality in a cell's internal regulatory mechanisms that results in uncontrolled growth and reproduction of the cell. Normal cells make up tissues, and when these cells lose their ability to behave as a specified, controlled, and coordinated unit, (termed "dedifferentiation"), the defect leads to disarray among the cell population. When this occurs, a tumor begins to propagate.

In addressing a cancerous condition, the essence of many medical treatments and procedures involves the removal or destruction of the tumor tissue. Examples of significant types of treatments include the surgical removal of cancerous growths and the destruction of metastatic tumors through chemotherapy and/or radiation therapy.

Surgery often is the first step in the treatment of cancer. The objective of surgery varies. Sometimes it is used to remove as much of the evident cancerous tumor as possible, or at least to "debulk" it (remove the major bulk(s) of tumor so that there is less that needs to be treated by other techniques). Depending on the type of cancer and its location, surgery can also provide some symptomatic relief to the patient. For example, if a surgeon can remove a large portion of an expanding brain tumor, the pressure inside the skull will decrease, leading to improvement in the patient's symptoms.

However, not all tumors are amenable to surgery. Some may be located in parts of the body that render them impossible to completely excise. Examples of these would include tumors in the brainstem (a part of the brain that controls breathing) or a tumor which has grown in and around a major blood vessel. In these cases, the role of surgery is limited due to the high risk associated with tumor removal.

In some cases, surgery is not employed to debulk a tumor because it is simply not necessary. An example is Hodgkin's lymphoma, a cancer of the lymph nodes that responds very well to combinations of chemotherapy and radiation therapy. In Hodgkin's lymphoma, surgery is rarely needed to achieve cure, but almost always used to establish a diagnosis (i.e. in the form of a biopsy).

Chemotherapy is another common form of cancer treatment. Essentially, it involves the use of medications (usually administered orally or by injection) which specifically attack rapidly dividing cells (such as those found in a tumor) throughout the body. This makes chemotherapy useful in treating cancers that have already metastasized, as well as tumors that have a high chance of spreading through the blood and lymphatic systems but are not evident beyond the primary tumor. Chemotherapy may also be used to enhance the response of localized tumors to surgery and radiation therapy. This is the case, for example, for some cancers of the head and neck.

Unfortunately, other cells in the human body that also normally divide rapidly (such as the lining of the stomach and hair) also are affected by chemotherapy. For this reason, many chemotherapy agents induce undesirable side effects such as nausea, vomiting, anemia, hair loss or other symptoms. These side effects are temporary, and there exist medications that can help alleviate many of these side effects. As knowledge in the medical arts has continued to grow, researchers have devised newer chemotherapeutic agents that are not only better at killing cancer cells, but that also result in fewer side effects for the patient.

As also discussed generally above, radiation therapy is another commonly used weapon in the fight against cancer. Ionizing radiation kills cancer by penetrating skin and intervening tissue, and damaging the DNA within the tumor cells. The radiation is delivered in different ways. The most common delivery technique involves directing a beam of radiation at the patient in a highly precise manner, focusing on the tumor. In performing this treatment, a patient lies on a table and the beam source moves around him or her, while transmitting the therapeutic radiation dose in a directed manner. The procedure lasts minutes, but may be performed daily for several weeks (depending on the type of tumor), to achieve a particular total prescribed dose. A radioisotope can be safely used to deliver local radiation for cancer treatment. A typical example of a radioisotope is I-131 for the treatment of thyroid cancer.

Another radiation method sometimes employed, called brachytherapy, involves implanting radioactive pellets (seeds) or wires in the patient's body in the region of the tumor. The implants can be temporary or permanent. For permanent implants, the radiation in the seeds decays over a period of days or weeks so that the patient is not rendered radioactive. For temporary implants, the entire dose of radiation is usually delivered in a few days, and the patient must remain in the hospital during that time, due to the need for observation and generally in view of his or her heightened radioactivity. For both types of brachytherapy, radiation is generally delivered to a very targeted area to gain local control over a cancer (as opposed to treating the whole body, as is accomplished using chemotherapy).

A number of other cancer therapies exist, although presently, the majority of such treatments are under exploration in clinical trials, and have not yet become a standard of care. Examples of such varied treatments include the use of immunotherapy, monoclonal antibodies, anti-angiogenesis factors and gene therapy. A brief description of each of these relatively new treatment regimes is as follows:

Immunotherapy: There are various techniques designed to assist the patient's own immune system fight the cancer, quite separately from radiation or chemotherapy. Oftentimes, to achieve the goal, researchers inject the patient with a specially derived vaccine that strengthens the particular immune response needed to resist the cancer.

Monoclonal Antibodies: These are antibodies designed to attach to cancerous cells (but not normal cells) by taking advantage of differences between cancerous and non-cancerous cells in their antigenic and/or other characteristics. The antibodies can be administered to the patient alone or conjugated to various cytotoxic compounds or in radioactive form, such that the antibody preferentially targets the cancerous cells, thereby delivering the toxic agent or radioactivity to the desired cells.

Anti-Angiogenesis Factors: As cancer cells rapidly divide and tumors grow, they can soon outgrow their blood supply. To compensate for this, some tumors secrete a substance believed to help induce the growth of blood vessels in their vicinity, thus providing the cancer cells with a vascular source of nutrients. Experimental therapies have been designed to arrest the growth of blood vessels to tumors, thereby depriving them of needed sustenance.

Gene Therapy: Cancer is the product of a series of mutations that ultimately lead to the production of a cancer cell and its excessive proliferation. Cancers can be treated by introducing genes to the cancer cells that will act either to check or stop the cancer's proliferation, turn on the cell's programmed cell mechanisms to destroy the cell, enhance immune recognition of the cell, or express a pro-drug that converts to a toxic metabolite or a cytokine that inhibits tumor growth.

Another option for treatment in certain types of cancers is to employ an isotope that is tailored to be taken-up by the particular organ or tissue. For example, Iodine 131 is employed to treat thyroid cancer. The thyroid cancer cells have hundreds more times the potential to attract in the radioactive Iodine I-131 than other cells. The Iodine isotope effectively kills cancer cells in the thyroid. Advantageously, the radioactive wave of I-131 does not travel far, so it does not kill the cells of other organs than thyroid tissue. This renders the administration of Iodine a safe treatment in thyroid cancer and over active thyroid disease, and it has been used in this context for decades. However, the use of a "raw" isotope is only applicable to organs and tissues that have an affinity for the underlying element. In general, most organs and tissues do not selectively uptake a particular element having a radioactive, yet short-distance-acting, isotope.

It is therefore desirable to provide a compound/agent and treatment method employing such a compound/agent, which destroys, and hence either facilitates the removal of or inhibits the further growth of tumor cells and tissue, while exhibiting mainly local effects and minimal or no systemic toxicity. This compound and treatment method should accomplish its goals in a manner that is free of significant damage to non-cancerous cells and that is highly selective for cancer cells. The compound and treatment method should also potentially be applicable to a wide variety of organs and tissues.

SUMMARY OF THE INVENTION

This invention overcomes the disadvantages of the prior art by providing a combination of a gene and isotope therapy that is applied to a cancerous tissue to selectively kill that associated cancer cells with minimal negative effects on surrounding non-cancerous cells. Illustratively, the compound/agent and associated treatment method combines molecular biology and nuclear medicine to provide an effective agent that selectively attacks cancerous tumors in a wide variety of organs and tissues.

Functionally, the specific DNA fragments with labeled isotope are able to bind the tumor cells DNA, and then the isotope kills the tumor cells. A gene is employed as a carrier to deliver the P-32 which can kill cancer cells through radioactive emission. Unlike traditional gene therapy, which employs a gene to express a protein, which can suppress the cancer cell growth or increase the sensitivity for radiation therapy or chemotherapy, the illustrative embodiment actually binds the radioactive substance via a gene. The illustrative embodiment produces the compound/agent containing a gene (DNA fragment) and P-32 through use of conventional P-32 labeling techniques such as those employed in molecular biology experiments (for example experiments used to test gene expression and gene amplification potency). In the illustrative embodiment, however, the same P-32 labeled DNA is employed directly for cancer treatment through a novel medical treatment method.

In an illustrative embodiment, the compound/agent is synthesized using conventional P-32 labeling techniques and an associated commercially available labeling kit that binds P-32 to a gene fragment appropriate to migrate into, and bind with, DNA of a tumor cell via recombination. Illustratively, the AFP gene is used because it is associated with certain types of tumor cells (in the liver, for example), such as the Huh7 cell types. An appropriate fragment length of the AFP gene is labeled with P-32. The fragment length is highly variable, amounting to between 10 base pairs (bp) to 2032 bp (which defines the complete sequence of AFP cDNA) in various embodiments. A plurality of different fragment lengths can also be combined in the compound/agent. In one embodiment of human treatment method an illustrative fragment length of 10-2032 bp can be used. However, in certain protocols, the range of fragment lengths can be more closely defined. In a human treatment method, the tumor is initially imaged to determine tumor size and characteristics. An initial dose of 1-160 mci (of radioactivity) is then administered depending upon tumor size and patient age and weight. The patient is observed to determine whether sufficient compound/agent has been administered, and if not, more is administered. After administration (typically 1-3 months subsequent) the patient's tumor is imaged to determine the prognosis. If prognosis is less than optimal, one or more additional administrations of the compound/agent can be undertaken. In another embodiment, illustrative compound and method can also be used in diagnosis of cancer and associated conditions. After administering an appropriate dose of the P-32 labeled DNA, a whole body scan can be applied to the patient within approximately 24 to 72 hours. Based upon the radioactivity of the P-32, which binds to the genomic DNA in the affected cells, the cancerous region is clearly visible in the nuclear scan.

In alternate embodiments, where the P-32 labeled DNA is to be employed in the treatment and/or diagnosis of other types of cancer, it is expressly contemplated that a gene fragment more-specific to the affected cells can be employed. For example if a cancer cell exhibits a different gene in elevated quantities, then a fragment with the ability to bind to that particular gene can be employed. The labeling of this alternate fragment can occur in accordance with conventional labeling procedures in an illustrative embodiment.

BRIEF DESCRIPTION OF THE DRAWINGS

The invention description below refers to the accompanying drawings, of which.

DETAILED DESCRIPTION

Figure 1:
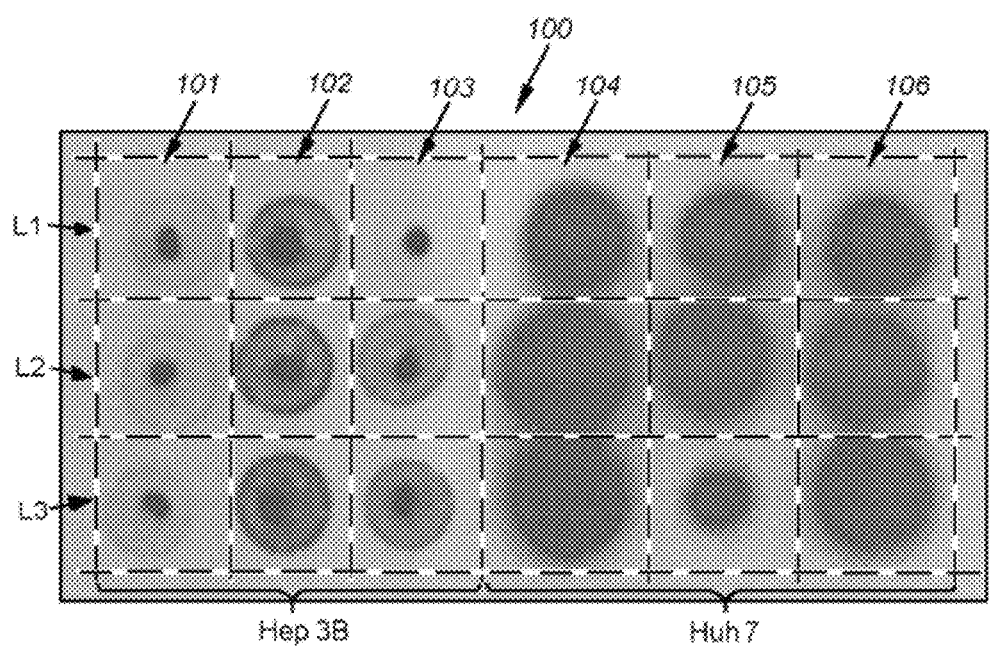
FIG. 1 is a photomicrographic diagram showing a dot-blot result associated with an arrangement of a plurality of Hep3B and Huh7 liver cells that have undergone treatment with a P-32 labelled compound/agent and depict various states of exposure based upon the treatment parameters.

A compound/agent and associated medical treatment method employing the compound/agent that selectively kills tumor cells using P-32 isotope carried on a DNA fragment is provided herein. Illustratively, the P-32 isotope is bound to a fragment of the alpha-fetoprotein (AFP) gene. In an illustrative embodiment, the term "fragment" is defined to include a sequence of contiguous base pairs (bp) ranging between approximately 10 bp to 2032 bp (the full length of the gene). The bonding of P-32 isotope is accomplished using conventional labeling techniques. The DNA fragment that is produced is employed as a carrier for P-32 isotope into cancer cells, so as to kill them through radiation emitted from the P-32 once the fragment is absorbed by the cell and bound to the cell's DNA.

I. Production of the Compound/Agent

The compound/agent can be generated for use by conventional processes using a predetermined fragment of plurality of different fragments of the AFP gene. The sequence of this gene is well known. In an embodiment, the fragments can be produced using a conventional PCR or DNA synthesis machine to produce the p-32 AFP DNA fragments, the DNA length designed as 10-2032 bps. The DNA fragments can be any part of the whole AFP DNA sequence. In an embodiment in which the compound/agent is employed as a probe to determine cell-uptake, as described further below, 50 ng (or another quantity) of AFP cDNA is 32p[alpha-dCTP]-labeled using random primed DNA labeling kit. The labeling product is then purified to exclude the unincorporated nucleotides. In an exemplary embodiment, length of the resulting purified P-32 AFP DNA is at least 20 bp, but other lengths are expressly contemplated as described above. Radioactivity of probe can then be quantified by scintillation counter. The associated counts per minute (cpm) of the P-32 labeled probe is determined by the scintillation counter. 1 ul of labeled reaction can be used for quantification in an exemplary embodiment.

II. Cell-Level Test of Compound/Agent Effectiveness

With a focus on liver cancer cells as an initial target, the goal of an initial test was to determine whether small fragments of AFP DNA are capable of migrating into liver cancer cells, binding to DNA and remaining bound for sufficient time periods. The first test relates to whether small AFP DNA fragments are capable of migrating into liver cancer cells efficiently.

Uptaking of 32p-labeled AFP DNA Fragments by Hep3B and Huh7 Hepatoma Cells:

A. Materials Employed
1. Cell lines: Hep3B and Huh7 hepatoma cell lines.
2. Radioactive materials: 32p[alpha-dCTP] (available from Perkin Elmer Life Sciences, Catalog No. BLU513H250uc).
3. Human alpha fetoprotein (AFP) plasmid (pCMV-sport6-AFP) (available from Open Biosystems, Catalog No. MHS1010-7430075)
4. Gel extraction kit (available from Qiagen: Catalog No. 20021)
5. Random primed DNA labeling kit (available from Roche USA, Catalog No. 11004760001)
6. G-50m Micro Columns (available from GE Healthcare; Catalog No. 28903408)
7. Transfection agent: FuGene
8. DNA isolation kit, DNAzol (available from Invitrogen, Catalog No. 10503-027)

B. Methods Employed
1. Perform PCR purification of all lengths of AFP cDNA:
   Using pCMV-sport6-AFP as the template, the whole length of AFP cDNA is PCR amplified by using the following pair of primers (P1, P2):

```
                                           (SEQ ID NO: 1)
   P1: CTAGCAACCATGAAGTGGGTGGAATCA;

(SEQ ID NO: 2)
   P2: CTTGGCAGCATTTCTCCAACAGGCCTGAG
```

2. Preparation of 32P-labeled AFP probe (as described also above):
   50 ng of AFP cDNA is 32p[alpha-dCTP]-labeled using a random primed DNA labeling kit. The labeling product is purified to exclude the unincorporated nucleotide. The length of purified probe is at least 20 bp.
3. Radioactivity of probe is quantified by a scintillation counter, thereby determining the cpm of labeled probe. 1 ul of labeled reaction is used for quantification.
4. Cell preparation and treatment with radio-labeled AFP probe in which the exponentially growing hepatoma cells (Hep3B and Huh7) are trypsinized one day before treatment and seeded on 24-well plate at the density of 6×104 cells per well. This well is not shown. However the arrangement is represented by the dot blot photomicrograph 100 in FIG. 1, where the genomic DNA from cells in each of the groups is arranged after treatment. The results from the treated cells are arranged in six lines (columns) 101-106. Columns 101-103 contain Hep3B cells and columns 104-106 contain Huh7 cells. There are three rows L1, L2 and L3 in the arrangement. Except as described below, the treatments are discretely provided to each of three cells (L1, L2 and L3) for each cell line (101-106):

Lines 101 and 104: 6 ul of 32p-labeled probe without adding any transfection reagent.

Lines 102 and 105: 6 ul of 32p-labeled probe with transfection agent following the proportion of 3 ul FuGene+2 ug 32P-labeled DNA. FuGene is a commercial regent which assists in allowing DNAs to migrate into cells.

Lines 103 and 106: 6 ul of radiolabeled probe with transfusion agent following the proportion of 8 ul FuGene+2 ug 32P-labeled DNA.

The cell at location 105, L3 was provided with 1 ul of 32p-labeled probe as a comparison to all other cells, which were provided with 6 ul of 32p-labeled probe.

6. The cells are incubated with radioactive probe for 12-16 hours. The genomic DNAs are then isolated from the cells by DNAzol. The incorporated radioactive DNA fragments into the genome are thereafter quantified by a scintillation counter. In addition, whole amount of genomic DNA samples are dot-blotted on the nylon membrane, and the membrane is exposed to a Kodak X-film, which provides the cellular-level image shown in FIG. 1.

C. Result and Conclusions of Cellular-Level Treatment:

The arrangement 100 in FIG. 1 shows the results of treatment of individual Hep3B cells (lines 101-102) and individual Huh7 cells (lines 104-106) using the various treatment parameters described in Section B above. The following are specific results based upon the exposed image of each cell and the detected cpm value:

1. As indicated partially by the extreme darkness of the exposure. Huh7 hepatoma cells can uptake 32p-labeled AFP fragments, but Hep3B hepatoma cells appear to uptake a minimal amount of 32p-DNA fragments. The difference is approximately 66 times greater in Huh7 than Hep3B. Some promise may be shown in the treatment of Hep3B cells of line 102. There is no significant difference between lines 104, 105 and 106.

2. A lower dose of AFP DNA (1 ul rather than 6 ul) results in less uptake, as shown by the cell at line 105, L3. This difference is significant based upon a count of 302 cpm for the lower dose cell, versus 7400 cpm. This shows that the uptake of DNA by the Huh7 cell is dose (of DNA) related.

3. The small AFP DNA fragments used can readily migrate into the cancer cells without using of a transfection agent, particularly in the case of Huh7.

4. The small AFP DNA fragments remain within the cancer cell so as to provide a desired dosage of ionizing radiation, which can be detected by dot blot.

5. More generally, based upon the radioactivity readings (count as cpm) of genomic DNA isolated from hepatocarcinoma cells after incubation with P-32 labeled AFP DNA fragments, the Huh7 cells can uptake P32-labeled AFP DNAs, which is not affected by adding FuGene. Hep3B cells are minimally able, or unable to uptake the DNAs. The result is significant based upon a determined difference in counts 111.3 vs 7400 (e.g. 66 times difference).

III. Live Animal Model Experiment: In Vivo Treatment for Liver Cancer

Based upon proof that small AFP DNA fragments can penetrate into liver cells using, or free-of, a transfection agent, a series of animal tests are performed on tumors. The following procedure steps are provided:

1. Prepare treatment compound/agent containing AFP DNA fragments and label the DNAs with P-32 isotope A. Materials Employed 1. AFP vector (dilute the plasmid to final concentration 50 ng/μl by water)

2. AFP Forward primer P1 and P2 (20 μmol) in H$_2$O, Reverse prime (20 μmol) in H$_2$O (from Invitrogen):

```
                                          (SEQ ID NO: 3)
P1 sequence (1521-    ACCCTGGTGTTGGCCAGTGCTG
1546):
                      CACT;

(SEQ ID NO: 4)
P2 sequence (1655-    TCTTGCTTCATCGTTTGCAGCG
1682):
                      CTACAC
```

3. DNA Labeling kit components:

| | |
|---|---|
| dATP | D4026A |
| dCTP | D4028A |
| dTTP | D4029A |
| dGTP | D4027A |

LA Tag DNA polymerase DRR02A (available from Takara Bio)

[α-P$^{32}$]dATP

[α-P$^{32}$]dCTP (available from Fu Rui Biotechnology, Beijing)

4. Illustra MicroSpin G-50 Columns (available from Amersham Pharmacia)

5. Mini-monitor (Morgen Series 900)

6. PCR thermal cycle (MJ Research PTC-200)

The above materials are handled and used in accordance with ordinary skill and the respective manufacturers' recommended procedures.

B. Compound/agent Production Method Using Materials

1. Prepare 0.1 mmol/L dCTP 0.1 mmol/L dATP by TE.

2. Prepare dNTP solution containing dTTP dGTP each at 10 mmol/L

3. Set up amplification radiolabeling reactions for 10 time repetition;

With each reaction containing:

| | |
|---|---|
| 10xLA buffer | 5 μl |
| 10 mmol/L dNTP | 1 μl |
| 0.1 mmol/L dCTP | 1 μl |
| 0.1 mmol/L dATP | 1 μl |
| Sense primer | 2 μl |
| Antisense primer | 2 μl |
| AFP template DNA | 50 ng/μl 1 1 |
| [α--(32)P]dATP | 5 μl (10 μci/μl) |
| [α--(32)P]dCTP | 5 μl (10 μci/μl) |
| LA Taq DNA polymerase | 0.4 μl |
| H$_2$O | 26.6 μl. |

4. Gently tap the side of the reaction tube to mix ingredients.

5. Set up reaction following the following sequence of thermal parameters and associated exposure times:
   1) 94° C. 3 min
   2) 94° C. 30 s
   3) 55° C. 30 s
   4) 72° C. 5 min
   Repeat step 5 from exposure times/settings (2) to (4) for 40 cycles 6. Remove the tubes from the thermal cycle (step 5). Then remove remaining unincorporated dNTPs and the oligonucleotide with G-50 columns according to the manufacture's manual.

7. Next, employ the series 900, mini-monitor to measure the yield and the specific activity of radiolabeled AFP DNA fragments.

C. Animal Trials

Once the associated radioactivity activity of the DNA fragments resulting from the process has been determined, the compound/agent is prepared into injection into live animals experience liver cancer tumors. Before injection, the preparation of animals with liver tumors is the next step in the testing process.

In an example, H22 cells are injected subcutaneously at the flunk area of the receipt mice. Kunming nu/nu mice, male 22-24 gm are used in an example. At each injection site, $1 \times 10^6$ of H22 liver cancer cells are injected subcutaneously into the nude mice at flunk area. The tumor nodules are noted 6 days after injection. The mice are divided into three groups: a control group, (A), which receives only an injection of normal saline in the same volume as other groups receiving the compound/agent (the number n of this group equals 11); a second group (B) receiving the P-32 isotope only 5 uci per mouse (n=10); and a group (C) that receives the P-32 labeled AFP DNA compound/agent 5 uci per mouse (n=8).

The saline, P-32 isotope and P-32 AFP DNA compound are each injected into the peritoneal cavity in mice for liver cancer treatment on the sixth day after H22 injection and notation of resulting tumors. Following injection of the cancer treatment, survival, tumor size and radioactivity in the tumor tissue were the endpoint outcome to study. In this trial, only a single injection is made.

The subject animals are then observed for two weeks, and thereafter euthanized for subsequent tumor study. Tumors are removed from surviving animals and are shown in the photographic diagram 200 of FIG. 2. The extracted tumors for each of three groups A, B and C are displayed in corresponding photographic diagram rows A, B and C. The following table also exhibits the measured results:

| Animal Test Group | Number of Deaths | Treatment | Tumor Weight (grams) | Tumor Weight-to-Body Average (%) | Radio-activity (cpm) |
|---|---|---|---|---|---|
| Group A | 3 | Saline only | 8.75 | 16.8 | — |
| Group B | 6 | P-32 only | 7.2 | 15.2 | 41 |
| Group C | 1 | P-32 AFP DNA | 5.47* | 12.23* | 123* |

*P < 0.01

The results show higher radioactivity detected in group C mice which are treated with P-32 AFP DNA. This result suggests The P-32 labeled AFP DNA can bind the cancer cells' DNA and maintain in the cells longer, so as to kill the cells via radiation exposure. Only one mouse has died in Group C, but three have died in group A and six have died in Group B. This result shows the best survival in the Group treated with P-32 labeled AFP DNA, and the worst survival in the P-32 treated group. More specific results now follow below. This result suggests that P-32 labeled AFP DNA fragment treatment significantly improves survival in liver cancer.

Group A mice treated with normal saline, have tumors (210 in FIG. 2) that are harvested on the fourteenth day of treatment. The average tumor weight on the fourteenth day is 8.75 grams, in which the tumor weight to body weight ratio averages 16.8%.

Group B mice treated with normal P-32, have tumors (220 FIG. 2) that are harvested on the fourteenth day of treatment. The average tumor weight on the fourteenth day is 7.2 grams, in which the tumor weight to body weight ratio averages 15.2%.

Group C mice treated with P-32 AFP DNA compound/agent, have tumors that are harvested on day $14^{th}$ of treatment. The average tumor weight on the $14^{th}$ days is 5.47 grams, in which the tumor weight to body weight ratio averages 12.23%.

The table shows the relative radioactivity based on radioactive count from the tumor tissue on the $14^{th}$ day. Notably, the count in the Group C tumors is significantly higher than that of group B, indicating that the tumors retained the agent with radioactive P-32 more effectively.

Figure 2:
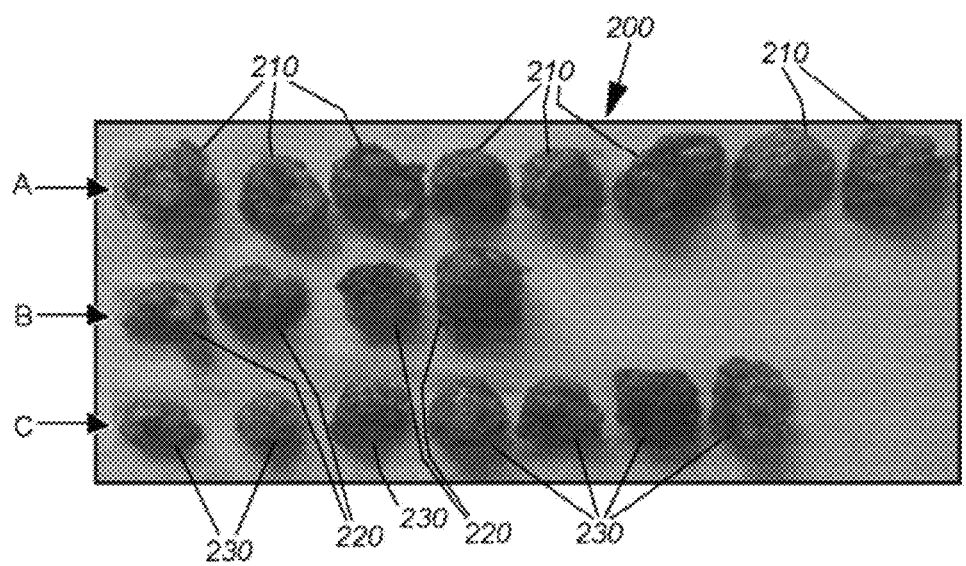
FIG. 2 is a photographic diagram of excised tumors obtained from three groups of animal test subjects, including a control group, a group injected with P-32 only, and a group injected with P-32 AFP DNA compound/agent according to an illustrative embodiment.

More generally, as depicted visually in FIG. 2, tumors in group C at the end point (14 days) are noticeably smaller than those of Group A and B. Combined with the measured radioactivity results, which is significantly higher in Group C than in Group B, the results overall suggest that the P-32 AFP DNA fragments binds with the tumor cells DNA and maintains the P-32 within the cancer cells longer.

Figure 3:
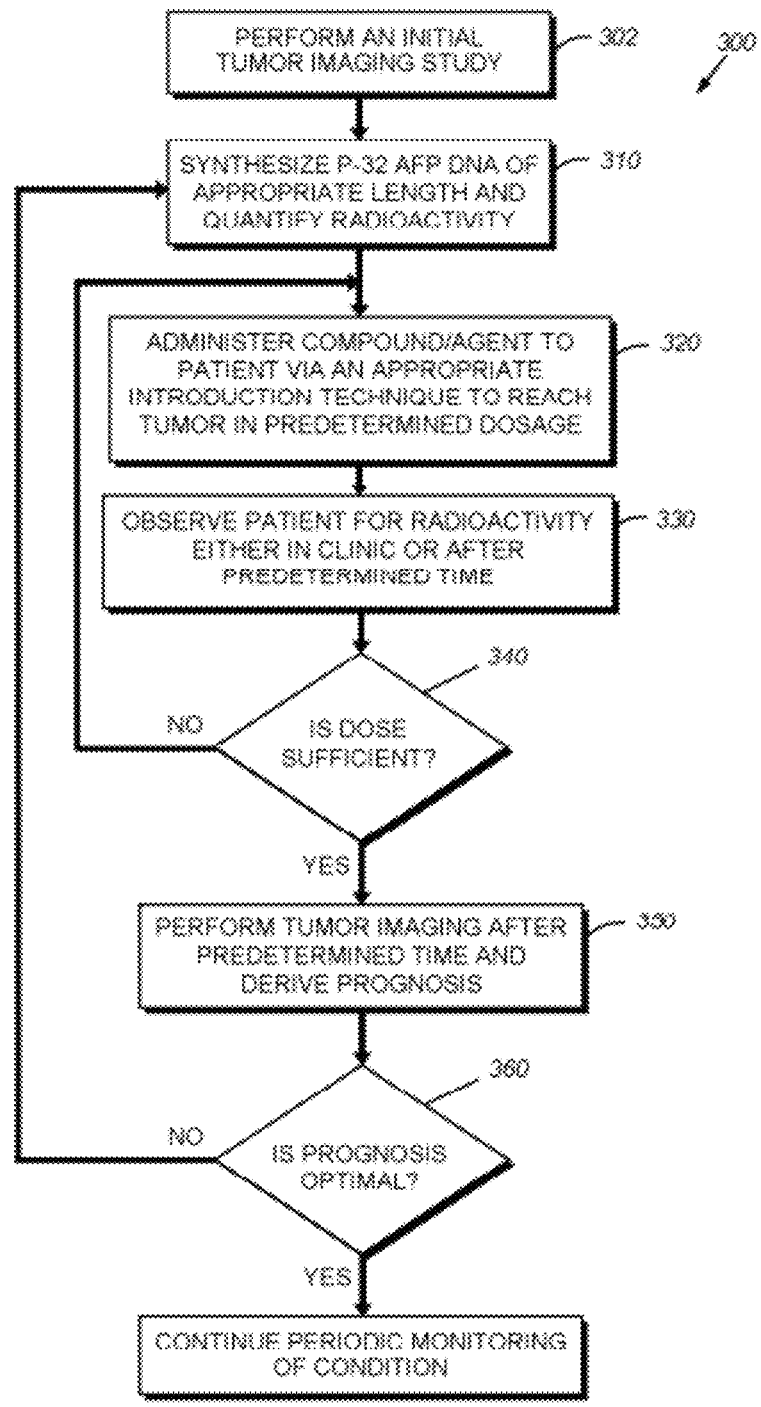
FIG. 3 is a flow diagram of a human medical treatment procedure employing the P-32 AFP DNA compound/agent according to an illustrative embodiment.

IV. Medical Treatment Method for Human Liver Cancer Treatment with Phosphorous-32 Labeled AFP DNA Fragments It is contemplated than an appropriate preparation of the above-described compound/agent including P-32 labeled AFP DNA can be employed in the medical treatment of liver cancer, and potentially other forms or cancer, in accordance with an associated treatment protocol. In an illustrative embodiment, the treatment method (as also shown in the flow diagram of FIG. 3) is as follows:

Patients selected for this treatment method (procedure 300 in FIG. 3) are typically those who have been diagnosed with liver cancer, and exhibit an elevated level of AFP. This treatment may better benefit the late stage liver cancer and/or with metastasis which are not amenable for surgery. Contraindication of radioactive therapy should be excluded from this treatment.

Desirably, before treatment begins, the each patient should undergo a tumor imaging study using an appropriate image modality or modalities (e.g. CT Scan, PET Scan, MRI, etc.) (step 302).

Using PCR or DNA synthesis machine to produce the P-32 AFP DNA fragments, the DNA length designed is between 10-2032 bp in an illustrative embodiment. The DNA fragments can be any part of the whole AFP DNA sequence, and it is expressly contemplated that a more-narrow size range can be defined in alternate embodiments. For example, if a certain size range of fragment is shown to more effectively penetrate a cell by experimentation, then that range of fragment sizes is selected for use in the compound. The materials to be used in synthesizing the compound/agent are as described in detail in Sections I-III above (step 310). The radioactivity of the compound/agent is quantified to assist in administering the proper dose.

A predetermined dosage—for example 1 to 160 mci of P-32 AFP DNAs are administered to each patient, illustratively by injecting the compound via the peritoneal cavity or administering it through angioplasty to liver vessels (artery, etc.) to target the tumor (step 320). The amount of administered radioactivity can be varied up and down 200% of the dose range as described above based on patient's age, body weight and the size of tumor. More generally, it is expressly contemplated that a wide variety of drug-delivery techniques and routes of delivery can be employed in any of the embodiments contemplated herein. For example the techniques for administering a predetermined dosage of the compound include, but are not limited to, delivery via (a) oral ingestion, (b) injection into a peritoneal cavity of the human body, (c) intravenously, (d) subcutaneously, (e) intramuscularly and (f) injection via a liver artery of the human body, (g) directly to the tumor tissue.

Each patient should be observed, typically in a special nuclear medicine ward (with radioactivity precautions in place) for one to three days, particularly if a higher dose (higher than 60 mci) is administered (step 330). If the dosage is insufficient (decision step 340) after initial observation, further compound/gent can be re-administered in an appropriate dosage (step 320), and the patient is re-observed (step 330). Once the patient has received the appropriate dosage, he or she can be discharged (via decision step 340). Precautions should be provided in detail upon discharge to the patient to avoid contamination of his or her direct environment—especially if small children are present.

A follow-up tumor imaging study is desirably performed one to three months after the treatment (step 350) for comparison with the pre-treatment study (step 302) to determine the effectiveness of the treatment. Based upon this examination, a prognosis can be derived by the practitioner.

Patients may require one or more follow-up treatments (injection of the P-32 DNA fragments and subsequent monitoring according to steps 310-360) to achieve optimal prognosis (decision step 360). When a desirable prognosis is achieved, the patient can be placed upon a less frequent, but still-diligent schedule of observation for recurrence of the condition (step 370).

V. Use of the Compound in a Diagnostic Procedure

It is also expressly contemplated that the illustrative compound and method can be employed to perform cancer diagnosis. In an illustrative embodiment the following steps are employed:

1. The P-32 labeled DNA fragment is administered to the patient in a manner similar to that described above for treatment. The dosage can vary as described above, potentially being lower, as the compound is being used in a diagnostic context, rather than a treatment context.

2. The patient is observed, potentially in a nuclear medicine ward for between approximately 24-72 hours after which time the compound has sufficiently and selectively bound to genomic DNA in the affected cancer cells. Alternatively, where the dose is sufficiently low, the patient may be released from the clinical environment during the relevant period and return for scanning 3. The patient is subjected to a whole body scan (or a localized scan where appropriate) typically between 24-72 hours after administration of the P-32 DNA fragment compound.

4. A practitioner (radiologist, etc.) studies the results of the scan to study regions where the tumor and/or metastasis exists in the patients body, these regions being highlighted in the scan based upon the P-32 emissions. Thereafter one or more practitioners perform a diagnosis of the studied condition for follow-up treatment.

It should be clear that the compound/agent described herein, as well as the illustrative medical treatment method employing the compound/agent provides a significant tool in the treatment of certain types of cancerous conditions. This method applies treatment selectively, and with minimal risk of over-exposure to radioactive substances.

The foregoing has been a detailed description of illustrative embodiments of the invention. Various modifications and additions can be made without departing from the spirit and scope of this invention. Each of the various embodiments described above may be combined with other described embodiments in order to provide multiple features. Furthermore, while the foregoing describes a number of separate embodiments of the apparatus and method of the present invention, what has been described herein is merely illustrative of the application of the principles of the present invention. For example, the size of the AFP fragment employed is highly variable, as is the portion of the overall fragment being employed for binding with P-32. The use of an AFP fragment is only one example of possible DNA strands that can be bound with P-32 for injection into cancerous tissue. It is contemplated that the medical treatment method herein can employ other types of DNA fragments that are shown to be associated with certain types of cancer cells. For example, the same methods described herein can be employed to label a calcitonin DNA fragment with P-32 to treat medullary thyroid carcinoma. Likewise a combination of different types of P-32 labeled fragments can be employed in a single injection to selectively bind with different portions of genes or different cell types in a tumor mass. Moreover, the use of the illustrative compound/agent in a treatment protocol can be supplemented with other forms of conventional treatment, such as chemotherapy, radiation, and the like, if needed to achieve the most desirable prognosis. Accordingly, this description is meant to be taken only by way of example, and not to otherwise limit the scope of this invention.

What is claimed is:

1. A medical treatment method for a tumor in a human body comprising the steps of:
    determining a condition of a liver cancer tumor in the human body;
    synthesizing a compound containing a linear, double-stranded DNA coding sequence of at least 20 base pairs (bp) labeled with P-32, the DNA fragment that selectively penetrates and is selectively uptaken by cancerous cells within the tumor and binding with genomic DNA within the cancerous cells;
    administering the compound so as to be delivered to the cancerous cells in a predetermined dosage, the dosage being sufficient to cause death of at least some of the cancerous cells through radiation provided by the P-32;
    monitoring the delivered dosage and repeating the step of administering as required; and
    re-determining the condition of the tumor after at least one step of administering to provide a prognosis,
    wherein the DNA comprises an AFP gene.

2. The medical treatment method as set forth in claim 1 wherein the predetermined dosage is between approximately 1 and 160 mci of radiation delivered.

3. The medical treatment method as set forth in claim 2 wherein the step of administering includes delivering the predetermined dosage of the compound through at least one of (a) oral ingestion, (b) via a peritoneal cavity of the human body, (c) intravenously, (d) subcutaneously, (e) intramuscularly and (f) via a liver artery of the human body and via direct injection to the tumor.

4. The medical treatment method as set forth in claim 1 wherein the DNA comprises a coding sequence of base pairs that is adapted to bind through recombination to an associated gene in genomic DNA that is prevalent in a predetermined type of cancer cell.

5. The medical treatment method as set forth in claim 4 wherein the predetermined dosage is between approximately 1 and 160 mci of radiation delivered.

6. The medical treatment method as set forth in claim 5 wherein the step of administering includes delivering the predetermined dosage of the compound through at least one of (a) oral ingestion, (b) via a peritoneal cavity of the human body, (c) intravenously, (d) subcutaneously, (e) intramuscularly and (f) via a liver artery of the human body and via direct injection to the tumor.

7. The medical treatment method as set forth in claim 1 wherein the predetermined dosage is between approximately 1 and 160 mci of radiation delivered.

8. The medical treatment method as set forth in claim 1 wherein the step of administering includes delivering the predetermined dosage of the compound through at least one of (a) oral ingestion, (b) via a peritoneal cavity of the human body, (c) intravenously, (d) subcutaneously, (e) intramuscularly and (f) via a liver artery of the human body and via direct injection to the tumor.

9. The medical treatment method as set forth in claim 8 wherein the DNA comprises a gene fragment.

10. The medical treatment method as set forth in claim 1 wherein the DNA comprises a gene fragment.

\* \* \* \* \*

SEQUENCE LISTING

```
<160> NUMBER OF SEQ ID NOS: 4

<210> SEQ ID NO 1
<211> LENGTH: 27
<212> TYPE: DNA
<213> ORGANISM: Homo sapiens

<400> SEQUENCE: 1
ctagcaacca tgaagtgggt ggaatca                                        27

<210> SEQ ID NO 2
<211> LENGTH: 29
<212> TYPE: DNA
<213> ORGANISM: Homo sapiens

<400> SEQUENCE: 2
cttggcagca tttctccaac aggcctgag                                      29

<210> SEQ ID NO 3
<211> LENGTH: 26
<212> TYPE: DNA
<213> ORGANISM: Homo sapiens

<400> SEQUENCE: 3
accctggtgt tggccagtgc tgcact                                         26
```

```
<210> SEQ ID NO 4
<211> LENGTH: 28
<212> TYPE: DNA
<213> ORGANISM: Homo sapiens

<400> SEQUENCE: 4
tcttgcttca tcgtttgcag cgctacac                                              28
```